United States Patent [19]

Brenman et al.

[11] Patent Number: 4,510,939

[45] Date of Patent: Apr. 16, 1985

[54] MEANS FOR TRANSFERRING ELECTRICAL ENERGY TO AND FROM LIVING TISSUE

[75] Inventors: Henry S. Brenman, Cinnaminson; Philip Katz, Princeton Junction; Mark Singer, Moorestown, all of N.J.

[73] Assignee: Biosonics, Inc., Philadelphia, Pa.

[21] Appl. No.: 452,319

[22] Filed: Dec. 22, 1982

[51] Int. Cl.³ .......................................... A61H 39/00
[52] U.S. Cl. .................................. 128/639; 128/800; 128/381; 128/741; 128/788
[58] Field of Search .............. 128/785, 788, 789, 796, 128/381, 24.1, 24.5, 800, 639, 774, 741

[56] References Cited

U.S. PATENT DOCUMENTS

| | | | |
|---|---|---|---|
| 206,474 | 7/1878 | Morel | 128/800 |
| 3,556,105 | 1/1971 | Shepard | 128/800 |
| 3,719,190 | 3/1973 | Avery | 128/785 |
| 3,845,771 | 11/1974 | Vise | 128/800 |
| 4,144,877 | 3/1979 | Frei et al. | 128/774 |
| 4,250,894 | 2/1981 | Frei et al. | 128/774 |

FOREIGN PATENT DOCUMENTS

| | | | |
|---|---|---|---|
| 2736102 | 8/1976 | Fed. Rep. of Germany | 128/774 |
| 0969374 | 12/1956 | France | 128/800 |

Primary Examiner—Lee S. Cohen
Assistant Examiner—Steven Falk
Attorney, Agent, or Firm—Robert C. Podwil

[57] ABSTRACT

A glove of thin, flexible elastomeric material carries electrodes, electrically connected to a connector disposed at the cuff of the glove, the connector permitting the electrodes to be electrically connected to a source of electrical energy or to a load, so that electrical energy may be applied to or drawn from living tissue.

12 Claims, 6 Drawing Figures

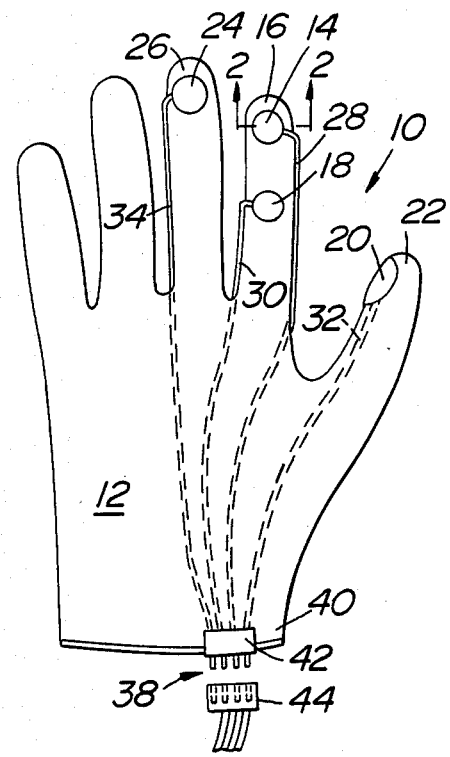
FIG. 1
FIG. 2
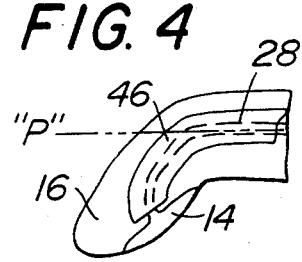
FIG. 4
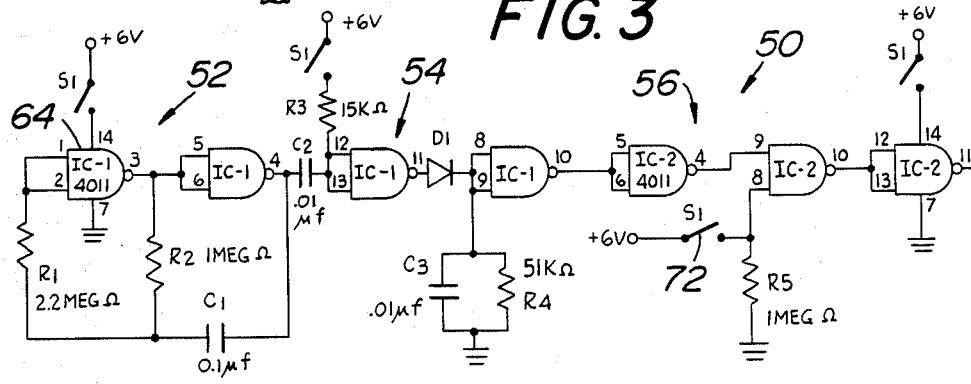
FIG. 3
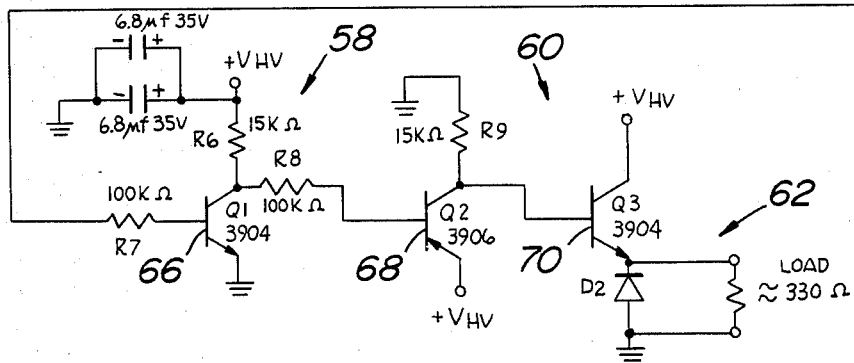

MEANS FOR TRANSFERRING ELECTRICAL ENERGY TO AND FROM LIVING TISSUE

BACKGROUND OF THE INVENTION

This invention relates to apparatus for applying electrical stimuli to living tissue, and more particularly, to apparatus for applying electrical stimuli for diagnostic purposes. In addition, this invention relates to apparatus for transferring electrical energy from living tissue to measuring, display and recording equipment used in operating rooms or physicians' offices.

In some medical procedures, it is useful or desirable to apply electrical energy to tissues of the body. For example, in connection with co-pending U.S. patent application Ser. No. 452,119, filed Dec. 22, 1982, for "APPARATUS AND METHOD FOR STIMULATING PENILE ERECTILE TISSUE", assigned to the assignee of the present application, the suitability of a particular candidate for use of the apparatus disclosed therein may be determined by palpation of the prostate gland, and the application of electrical energy to that gland so as to simulate the action of the apparatus. Similarly, the locations of critical regions or spots on the prostate gland can be determined by applying electrical energy to the prostate gland from a generator via the apparatus to the living tissue. The regions or spots at which a desired reaction, in that instance incipient erection, is stimulated, can thus be identified. Further, in connection with the above application, topical application of electrical energy to the anal area is desirable to induce contraction of the musculature of the rectum as an aid to intimately fitting a device to the rectal cavity.

It is, therefore, one object of this invention to provide apparatus for applying electrical stimuli to living tissue for diagnostic purposes.

Other diagnostic procedures involve the transference of electrical energy from tissues to recording devices. In cardiology, for example, certain diagnostic techniques involve the receipt of low voltages produced by the heart, and transferring these voltages to recording or display devices, as in cardiac mapping.

Another object of this invention is to provide an apparatus which is inexpensive to manufacture, easy to use, and which is of such a nature that it is disposable after usage.

SUMMARY OF THE INVENTION

Other objects will appear hereinafter.

The foregoing and other objects are realized, in a presently preferred form of the apparatus, by mounting on a glove of natural or synthetic rubber or rubber-like elastomeric material, one or more electrodes for applying energy to the tissues or for receiving energy from them. Also mounted on the glove are electrical conductors connecting the electrodes to an electrical connector which serves to couple the apparatus to a source of electrical energy or amplifying or display devices. The source of electrical energy may be a signal generating circuit, or simply a source of electrical potential, as the application may require. The electrodes and associated conductors may, in the presently preferred form of the apparatus, be applied to the glove by electrodeposition or other means, so as not to impede the normal flexibility of the glove or to render the glove less useful for normal palpation than conventional gloves, not fitted with electrodes and conductors.

There are seen in the drawings forms of the invention which are presently preferred (and which present the best mode contemplated for carrying the invention into effect), but it should be understood that the invention is not limited to the precise arrangements and instrumentalities shown.

DESCRIPTION OF DRAWINGS

FIG. 1 is a plan view of the palmar aspect of a glove incorporating the principles of the present invention.

FIG. 2 is a cross-sectional view, taken along the line 2—2 in FIG. 1.

FIG. 3 is a schematic diagram illustrating exemplary electronic circuit means, which may be used to generate a signal for use with the present apparatus.

FIG. 4 is a partial side elevation view, illustrating an aspect of the invention.

DETAILED DESCRIPTION

Figure 5:
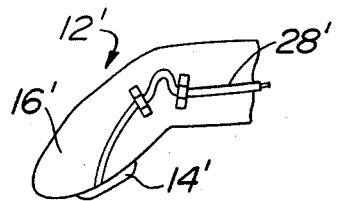
FIG. 5 is a partial side elevation view, illustrating an alternative form of the invention.

Referring now to the drawings in detail, wherein like reference numerals indicate like elements, there is seen in FIG. 1 apparatus designated generally by the reference numeral 10.

The apparatus 10 includes a glove 12, of natural or synthetic rubber or rubber-like elastomeric material. The glove 12, but for the special features to be described below, may be a conventional surgical glove of the wellknown and readily available kind. Such gloves are "thin", in the sense that they are so designed as to allow for a sensitive "feel" through their material, and highly flexible so as not to impede to any significant degree the manual dexterity of a wearer. Disposed upon the glove 12 are a plurality of planar electrodes whose shape may conform to that of a user's finger. In FIG. 1, for example, an electrode 14 is disposed beneath the distal phalange of the index finger 16. An electrode 18 is disposed approximately beneath the joint between the middle and proximal phalanges of the index finger 16. A third electrode 20 is disposed adjacent the end of the thumb 22. Another electrode 24 is disposed beneath the distal extremity of the phalange of the middle finger 26.

Referring again to FIG. 1, it will be seen that the various electrodes are electrically connected to conductors, such as the illustrated conductors 28, 30, 32 and 34. In the illustrated form of the apparatus 10, the conductor 28 is associated with the electrode 14; the conductor 30 is associated with the electrode 18; the conductor 32 is associated with the electrode 20; and the conductor 34 is associated with the electrode 24. Numerous other specific arrangements will occur to those skilled in the art.

As is apparent from FIG. 1, the conductors 28, 30, 32 and 34, like the electrodes themselves, are affixed to the external surface of the glove 12. The electrodes 14, 18, 20 and 24 and the respective conductors 28, 30, 32 and 34 may advantageously be applied by known techniques of electro- or chemical deposition, or may be pre-deposited on a substrate, such as Mylar, and then attached to the glove 12 by suitable adhesives. The material of the electrodes 14, 18, 20 and 24 and the conductors 28, 30, 32 and 34 may be platinum or another suitable conductive, inert, non-polarizing material.

After application of the conductors to the glove 12, an insulating overlayer (see in FIG. 4 but omitted elsewhere), such as the insulating strip 46 seen in FIG. 4, may be applied over them to limit electrical contact with the subject to the areas of the electrodes.

Referring to FIG. 4, the preferred location for the conductors 28, 30, 32 and 34, where they pass along the fingers of the glove 12, is on or near a lateral plane ("P") passing through a medial axis of the finger of the glove 12. When so disposed, the conductor 28 is subjected to a minimum of stretching in an axial direction, and thus exhibits maximum durability and least susceptibility to damage due to flexing of the glove 12 and finger.

Referring again to FIG. 1, the conductors 28, 30, 32 and 34 run from the respective electrodes 14, 18, 20 and 24 to one-half of a multiple pin type connector 38, secured to the cuff 40 of the glove 12. The connector 38 typically comprises two snap or frictionally interengageable parts 42 and 44, provided, respectively, with male and female elements. Other suitable connectors may be used. The elements may be so connected to the electrodes as to render selected electrodes functional in a given situation. For example, for certain palpation procedures and applications, such as the diagnostic technique set forth in the above-identified co-pending application, it may be desirable to use the electrode 14 as an active or stimulating electrode, and the electrodes 20 and 24 as "return" or ground electrodes. In such a situation, it is feasible to apply stimulating voltage only to those elements of the connector 38 which are electrically connected to the conductor 28, and to connect the conductors 32 and 34 associated, respectively, with the electrodes 20 and 24, to a return or ground wire.

Referring now to FIG. 5, there is seen an alternative form of the apparatus 10, in which elements corresponding to those previously described are designated by like primed (') reference numerals. The form of the apparatus 10 illustrated in FIG. 5 employs as the electrode 14' (which is representative of the other electrodes) a solder-filled dish-shaped disc of platinum or other appropriate material, affixed to the glove 12' by a suitable adhesive. Such electrodes, unlike those described above, are rigid. The electrode 14', and other electrodes (not shown in the figure) are electrically connected to an insulated wire 28' affixed to the glove 12' and associated with a connector (not shown) like the above-described connector 38.

Figure 6:
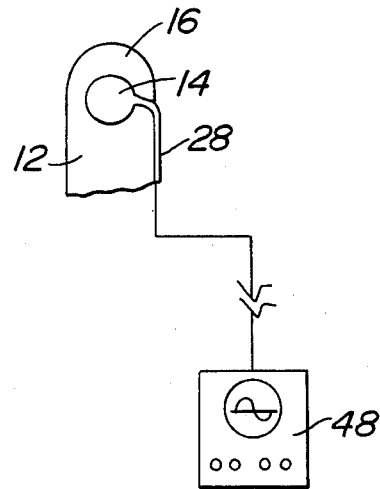
FIG. 6 is a schematic view, illustrating diagrammatically an application of the present invention in which electrical energy is received from tissue and represented on a display device.

FIG. 6 illustrates, somewhat diagramically, the manner in which the present invention may be used for transferring electrical energy from living tissue to measuring, displaying and recording equipment. In FIG. 6, the glove-mounted electrode 14 is shown, schematically, as an input for an oscilloscope 48. Thus, just as the electrode 14 may be used to apply electrical stimuli in certain procedures, it may also be used as a receptor of electrical energy from certain tissues.

FIG. 3 illustrates an example of an electronic circuit by which a stimulating signal can be produced for diagnostic purposes, although numerous other specific sources of potential or signal generators may be used in conjunction with the apparatus 10. The illustrated circuitry, designated generally by the reference numeral 50, includes an astable multivibrator, designated generally by the reference numeral 52; a monostable multivibrator, designated generally by the reference numeral 54; NAND gating 56; a pair of inverters 58 and 60; and an emitter-follower 62 providing a stimulating voltage (about 20 volts) output.

A power supply, now shown, may provide the signal generator circuitry 50 with logic level voltage (approximately 6 v. D.C.) and stimulating level voltage (approximately 24 v. D.C.) inputs, the logic level voltage inputs serving to power the circuitry 50 and the signal level voltage inputs providing the signal to be applied through selected electrodes.

The astable multivibrator 52 and monostable multivibrator 54, which comprise the first and second stages of the circuitry 50, provide pulses of logic level voltage and of a desired pulse-width and frequency. In the illustrated circuitry 50, the astable multivibrator 52 produces a series of square pulses at an amplitude of about 6 volts and a frequency of about 30 to 33 Hz, and the monostable multivibrator 54 serves to shape the pulses to a presently preferred width of 500 microseconds.

The principal components of the illustrated astable and monostable multivibrators 52, 54 are commercially available integrated circuits. The integrated circuit 64, for example, in FIG. 3, and the other integrated circuits labeled "IC-1" and "IC-2", may be CMOS No. 4011 integrated circuits available from numerous manufacturers, including, among others, RCA, Texas Instrument Corp., National Semiconductor, and Solid State Scientific. All of the other components in the illustrated circuitry 50 are also commercially available items. The NPN transistor 66 used in the inverter circuit 58 may be of the 2N 3904 type. The PNP transistor 68 in the inverter circuit 60 may be of the 2N 3906 type. The NPN transistor 70 in the emitter-follower 62 may also be of the 2N 3906 type.

Operation of the switch 72 applies to the astable multivibrator 52, monostable multivibrator 54, and other aspects of the circuitry 50, the logic voltage supply. An output pulse will be repetitively supplied during the time in which the circuitry 50 is so powered. In other words, output is enabled by closing of the switch 72, and inhibited when the switch 72 is open. The output of the circuitry illustrated in FIG. 3 may be applied to the connector 38, and through the connector 38 to the electrodes 14, 18, 20 and 24. The switch 72 enables the glove 12 to be used for palpation or to be otherwise positioned with assurance that the circuitry 50 is inhibited, thus eliminating undesirable effects such as untimely or unwanted stimulation affecting extraneous tissues. In the circuitry 50, when the output pulse is inhibited, the output is zero volts. When the output is enabled, the actual output level is a function of the voltage of the stimulating voltage supply. In one operative embodiment, the stimulating voltage supply provides about twenty-four volts, and the output is within 0.5 volts of this voltage and substantially constant for 500 microseconds when driving a 330 ohm load.

The present invention may be embodied in other specific forms without departing from its spirit and essential attributes and, accordingly, reference should be made to the appended claims rather than the foregoing specifications as indicating the scope of the invention.

What we claim is:

1. Apparatus for selectively transferring electrical energy to and from critical localities in living tissue for diagnostic purposes, comprising a glove of flexible fluid impervious elastomeric material, said material being sufficiently thin and flexible to afford to the wearer substantially unimpeded feel and manual dexterity so as to enable use of said glove for digital palpation while transferring energy to and from tissue, an electrode affixed to the index finger of said glove and covering the area of the glove beneath the tip of the distal phalange of the index finger of a wearer of said glove, thereby to facilitate application of said electrode directly to a palpated locality of tissue, a second electrode disposed adjacent to the tip of the thumb of said glove, an electrical connector coupled to said glove and adapted to be electrically connected to electrical circuitry external to said glove, and a plurality of flexible electrical conductors adhesively coupled to said glove and electrically connecting said electrodes and said connector.

2. Apparatus in accordance with claim 1, wherein said electrodes and said conductors comprise flexible films of electrically conductive material affixed to the surface of said glove.

3. Apparatus in accordance with claim 1, and a third electrode affixed to the middle finger of said glove and covering an area on said middle finger beneath the tip of the distal phalange of the middle finger of a wearer, thereby to facilitate the application of said last-mentioned electrode directly to a locality palpated by said middle finger.

4. Apparatus in accordance with claim 3, wherein said electrodes and said conductors comprise flexible films of electrically conductive material affixed to the surface of said glove.

5. Apparatus in accordance with claim 4, wherein portions of said conductors extend along the fingers of said glove, said portions being so disposed on the fingers as to be adjacent a medial plane passing laterally through the fingers, so that stretching of said conductors is minimized, and insulating means overlying said conductors.

6. Apparatus in accordance with claim 1, and a third electrode on said index finger of said glove, said third electrode being disposed approximately beneath the joint between the middle and proximal phalanges of the index finger of a wearer, thereby to facilitate the application of pressure by said joint.

7. Apparatus in accordance with claim 6, wherein said electrodes and said conductors comprise flexible films of electrically conductive material affixed to the surface of said glove.

8. Apparatus in accordance with claim 7, wherein portions of said conductors extend along the fingers of said glove, said portions being so disposed on the fingers as to be adjacent a medial plane passing laterally through the fingers, so that stretching of said conductors is minimized.

9. Apparatus in accordance with claim 1, and a third electrode on the index finger of said glove, said third electrode being disposed beneath the joint between the middle and proximal phalanges of the index finger of a wearer, thereby to facilitate the application of pressure on said third electrode by said joint, and a fourth electrode affixed to the middle finger of said glove and covering an area thereon beneath the tip of the distal phalange of the middle finger of a wearer, thereby to facilitate the application of said last-mentioned electrode directly to a locality palpated by said middle finger.

10. Apparatus in accordance with claim 9, wherein said electrodes and said conductors comprise flexible films of electrically conductive material affixed to the surface of of said glove.

11. Apparatus in accordance with claim 10, wherein portions of said conductors extend along the fingers of said glove, said portions being so disposed on the fingers as to be adjacent a medial plane passing laterally through the fingers, so that stretching of said conductors is minimized.

12. Apparatus in accordance with claim 11, wherein said electrical connector is coupled to said glove adjacent to the cuff.

* * * * *